(12) United States Patent
Chakrabarti

(10) Patent No.: US 9,532,972 B2
(45) Date of Patent: Jan. 3, 2017

(54) INCREASING TAXANE SENSITIVITY IN CANCER CELLS

(71) Applicant: Ratna Chakrabarti, Winter Springs, FL (US)

(72) Inventor: Ratna Chakrabarti, Winter Springs, FL (US)

(73) Assignee: UNIVERSITY OF CENTRAL FLORIDA RESEARCH FOUNDATION, INC., Orlando, FL (US)

( * ) Notice: Subject to any disclaimer, the term of this patent is extended or adjusted under 35 U.S.C. 154(b) by 0 days.

(21) Appl. No.: 14/376,704

(22) PCT Filed: Feb. 7, 2013

(86) PCT No.: PCT/US2013/025214
§ 371 (c)(1),
(2) Date: Aug. 5, 2014

(87) PCT Pub. No.: WO2013/119864
PCT Pub. Date: Aug. 15, 2013

(65) Prior Publication Data
US 2015/0030610 A1    Jan. 29, 2015

Related U.S. Application Data

(60) Provisional application No. 61/596,025, filed on Feb. 7, 2012.

(51) Int. Cl.
*C12N 15/113* (2010.01)
*A61K 31/337* (2006.01)
*A61K 31/427* (2006.01)
*A61K 31/7105* (2006.01)
*A61K 31/713* (2006.01)
*A61K 39/395* (2006.01)

(52) U.S. Cl.
CPC .......... *A61K 31/337* (2013.01); *A61K 31/427* (2013.01); *A61K 31/713* (2013.01); *A61K 31/7105* (2013.01); *A61K 39/39558* (2013.01); *C12N 15/1137* (2013.01); *C12Y 207/1101* (2013.01); *C12N 2310/14* (2013.01); *C12N 2310/141* (2013.01); *C12N 2310/531* (2013.01); *C12N 2320/31* (2013.01)

(58) Field of Classification Search
None
See application file for complete search history.

(56) References Cited

U.S. PATENT DOCUMENTS

| | | |
|---|---|---|
| 5,693,666 A | 12/1997 | Chen et al. |
| 5,912,263 A | 6/1999 | Menichincheri et al. |
| 5,994,576 A | 11/1999 | Holton et al. |
| 5,998,656 A | 12/1999 | Holton et al. |
| 6,028,005 A | 2/2000 | Jin |
| 6,136,808 A | 10/2000 | Abe et al. |
| 6,147,234 A | 11/2000 | Holton et al. |
| 6,509,370 B1 | 1/2003 | Joshi-Hangal et al. |
| 6,538,020 B2 | 3/2003 | Joshi-Hangal et al. |
| 6,541,508 B2 | 4/2003 | Ekwuribe et al. |
| 6,569,459 B2 | 5/2003 | Flashner-Barak |
| 6,649,777 B2 | 11/2003 | Holton et al. |
| 6,680,877 B1 | 1/2004 | Lienau |
| 6,939,978 B2 | 9/2005 | Chang et al. |
| 7,060,724 B2 | 6/2006 | Li et al. |
| 8,415,315 B2 | 4/2013 | Chakrabarti |
| 2009/0136957 A1* | 5/2009 | Ivanovska ............ C12N 15/113 435/6.12 |
| 2009/0175868 A1* | 7/2009 | Ludwig et al. ............ 424/138.1 |
| 2010/0029649 A1* | 2/2010 | Wrobleski et al. ........ 514/235.8 |
| 2010/0183604 A1* | 7/2010 | Ohta ...................... C07K 16/32 424/133.1 |

FOREIGN PATENT DOCUMENTS

WO    2010/135662    11/2010

OTHER PUBLICATIONS

Schratt et al. Nature 2006, vol. 439, pp. 283-289.*
Ottman, R. et al., "Abstract 3613:Down regulation of LIM kinase 1 enhances taxane sensitivity of cancer cells", Cancer Research 2011, vol. 71, Issue 8, Supplement 1 (abstract).
Ross-MacDonald, P. et al., "Identification of a nonkinase target mediating cytotoxicity of novel kinase inhibitors", Molecular Cancer Therapeutics, 2008, vol. 7, No. 11, pp. 3490-3498.
Davila, M. et al., "Expression of LIM kinase 1 is associated with reversible G1/S phase arrest, chromosomal instability and prostate cancer", Molecular Cancer, 2007, vol. 6, 12 pages.
Kwiatkowski, N. et. al, "Selective aurora kinase inhibitors identified using a taxol-induced checkpoint sensitivity screen", ACS Chemical Biology, Jan. 2012, vol. 7, pp. 185-196.

* cited by examiner

*Primary Examiner* — Tracy Vivlemore
(74) *Attorney, Agent, or Firm* — Timothy H. Van Dyke; Beusse, Wolter, Sanks & Maire, PLLC

(57) ABSTRACT

Disclosed herein are combinatorial therapies for treating or preventing reoccurrence of cancer. The therapies involve inhibition of LIMK1 in conjunction with taxane therapy. Specifically exemplified herein is co-administration of a LIMK1 RNA interfering molecule along with administration of a taxane.

4 Claims, 15 Drawing Sheets

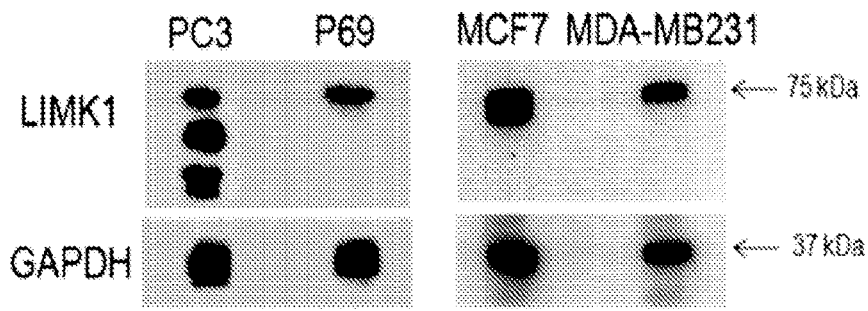
FIG. 1 A
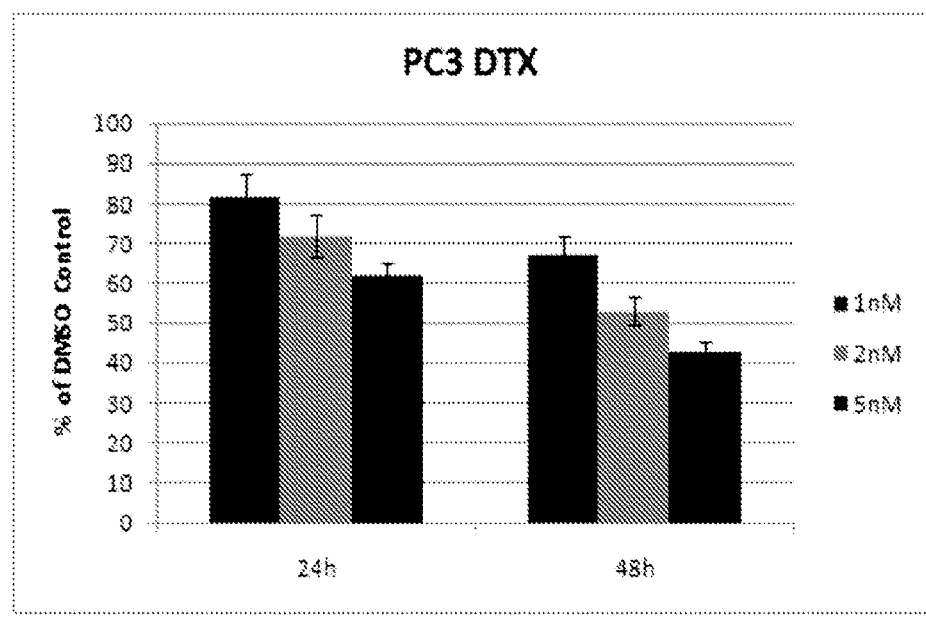
FIG. 1 B
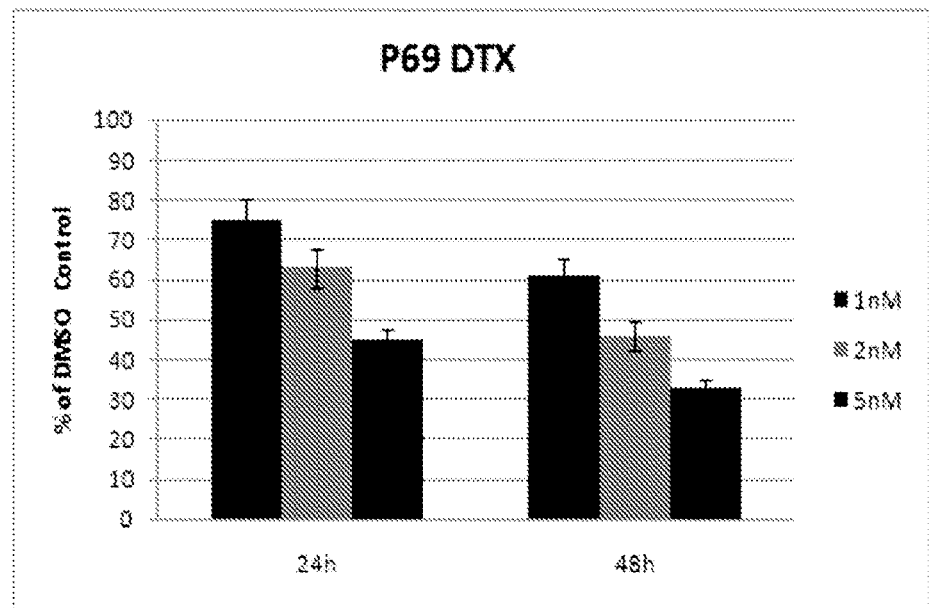

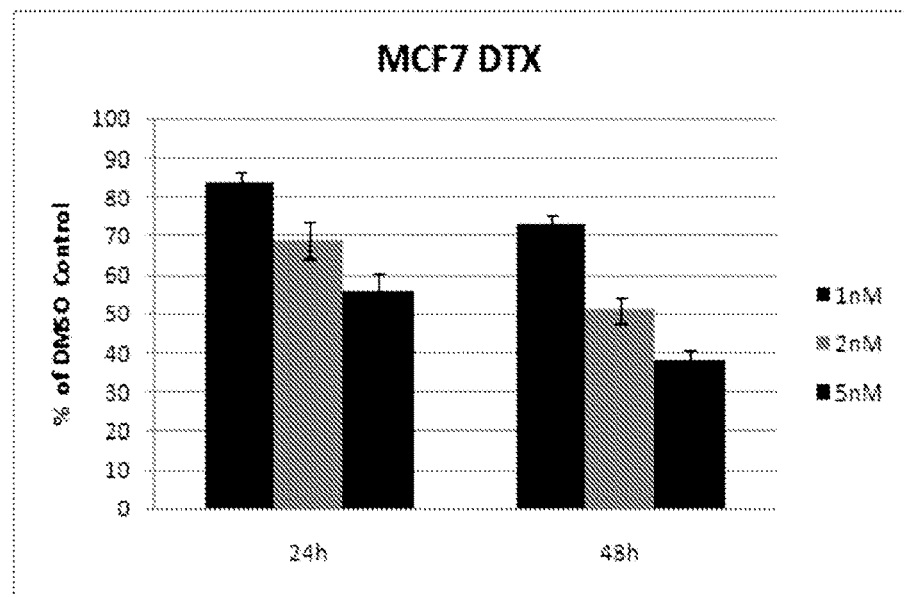
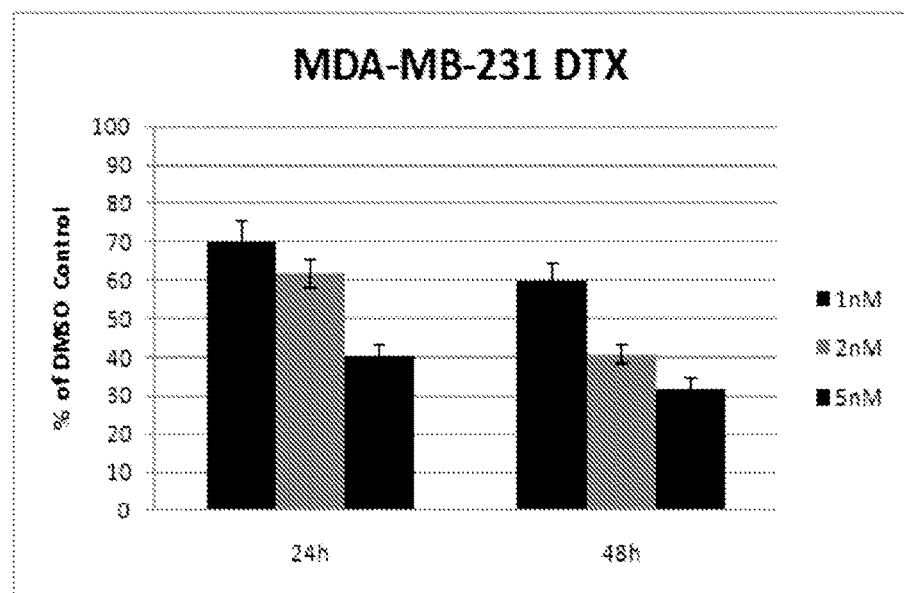
FIG. 1 B) cont.

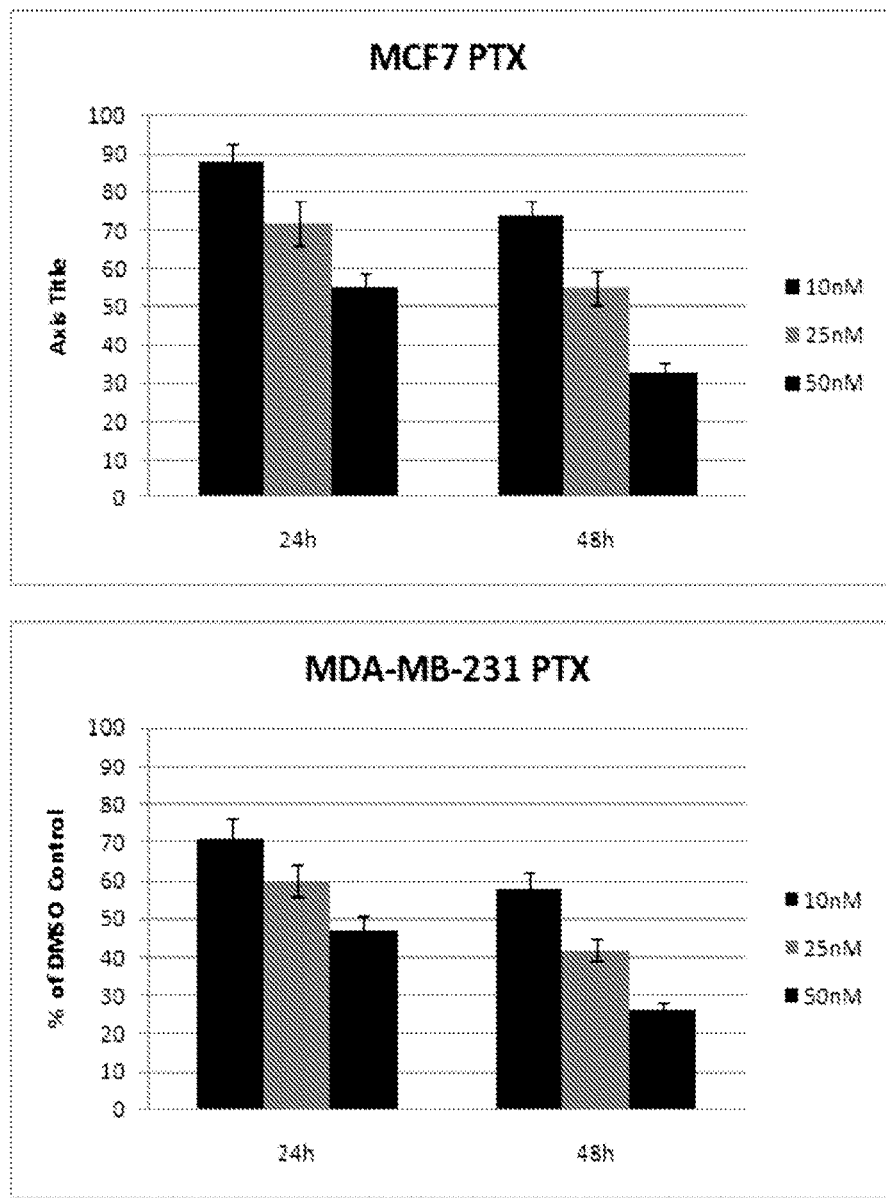
FIG. 1 C) Cont.

2D Flow Cytometry: Cell lines were treated with 2nM Docetaxel or DMSO for 12hrs and 24hrs. Following treatment cells were fixed, permeabilized, then stained with propidium iodide to monitor DNA content.

Graphical analysis of average cell cycle populations following 24hrs of 2nM Docetaxel treatment, depicted as a percentage of total cell number.

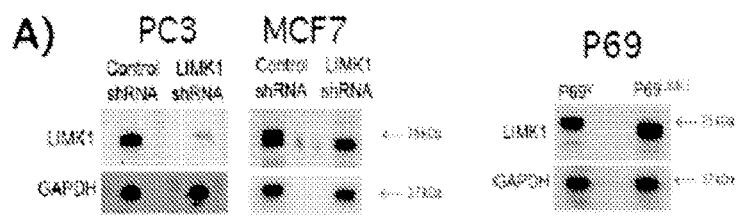
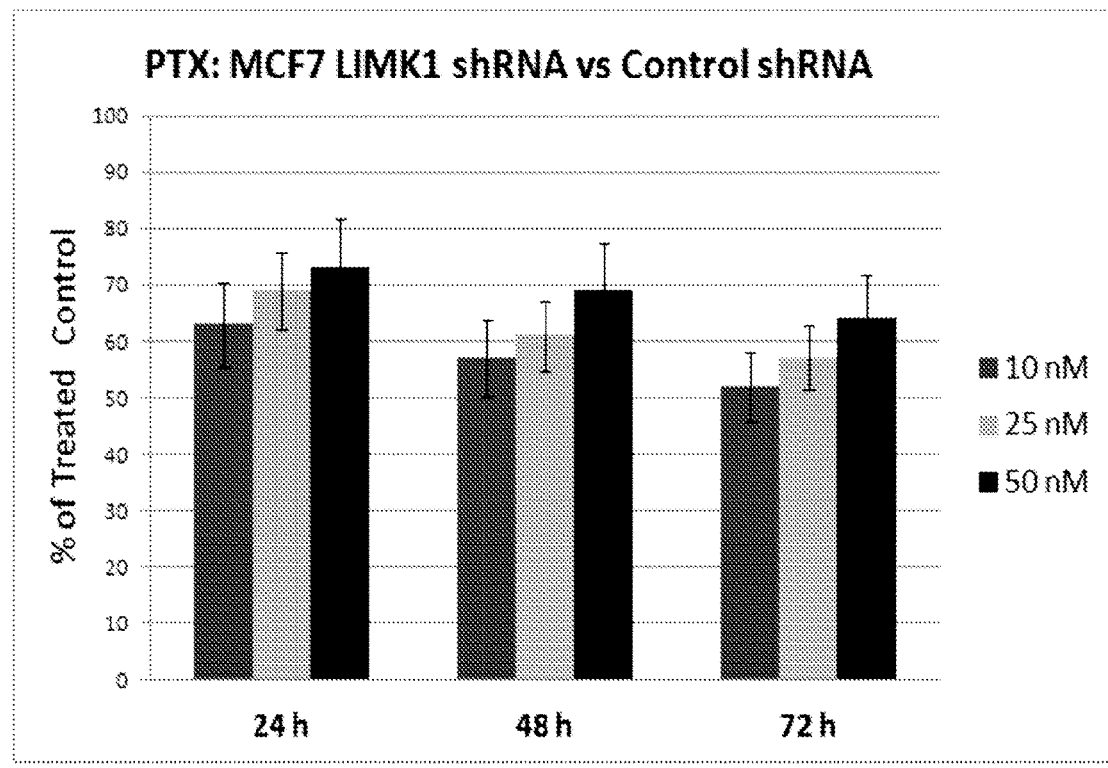
FIG. 3

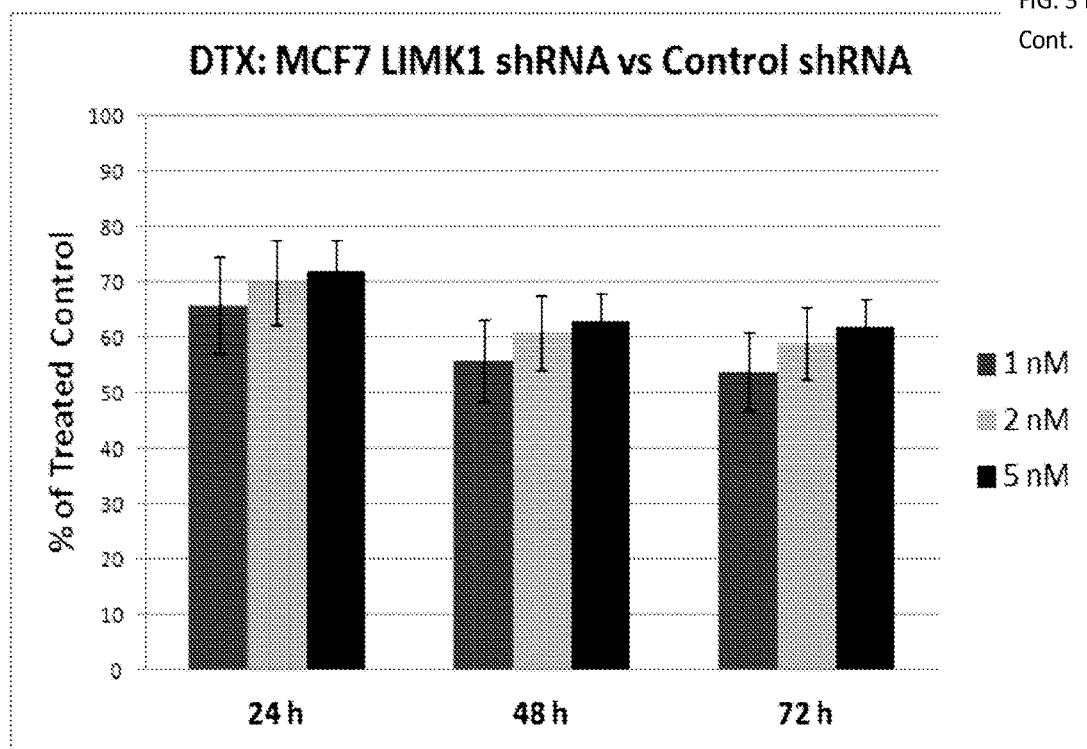
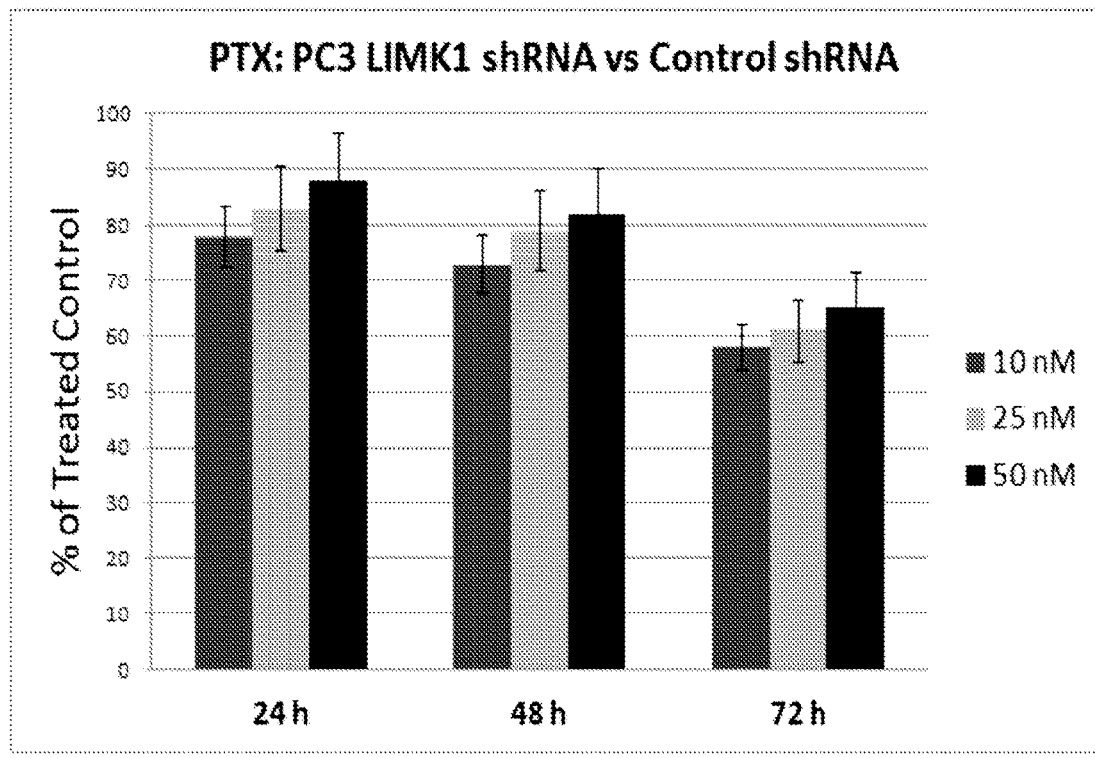
FIG. 3 B) Cont.

FIG. 3 B) Cont.
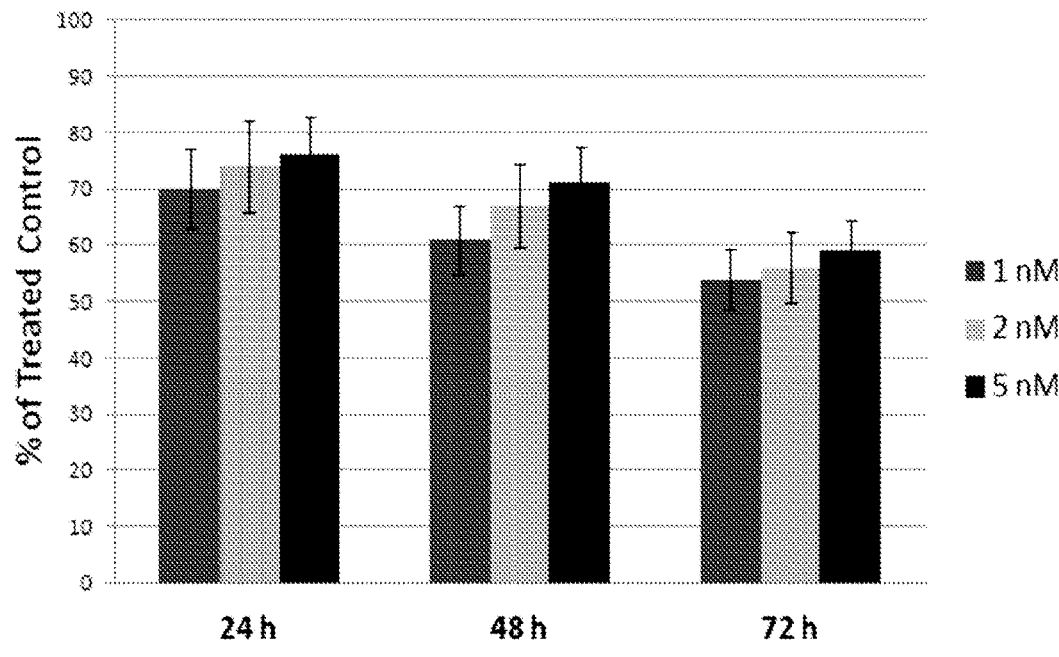
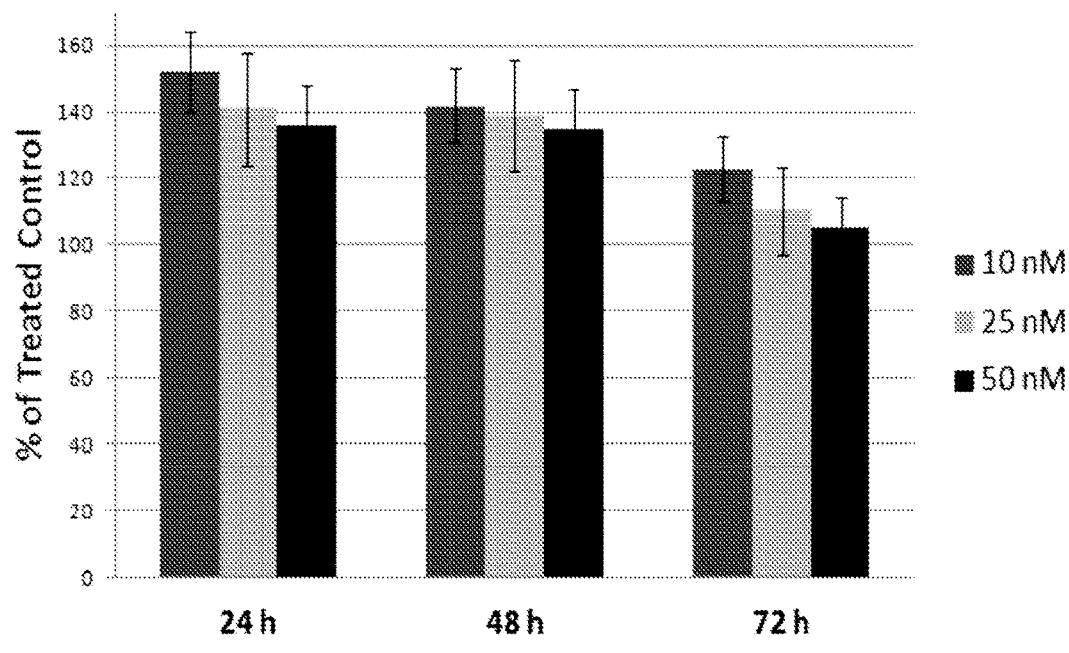

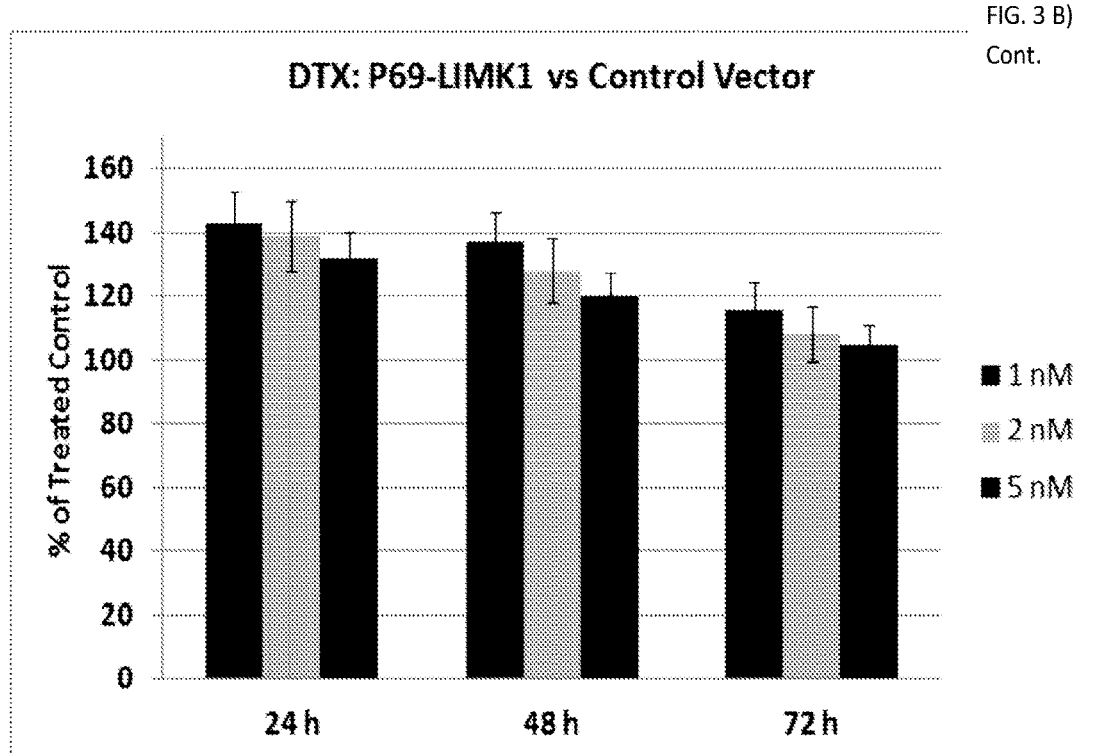
FIG. 3 B) Cont.

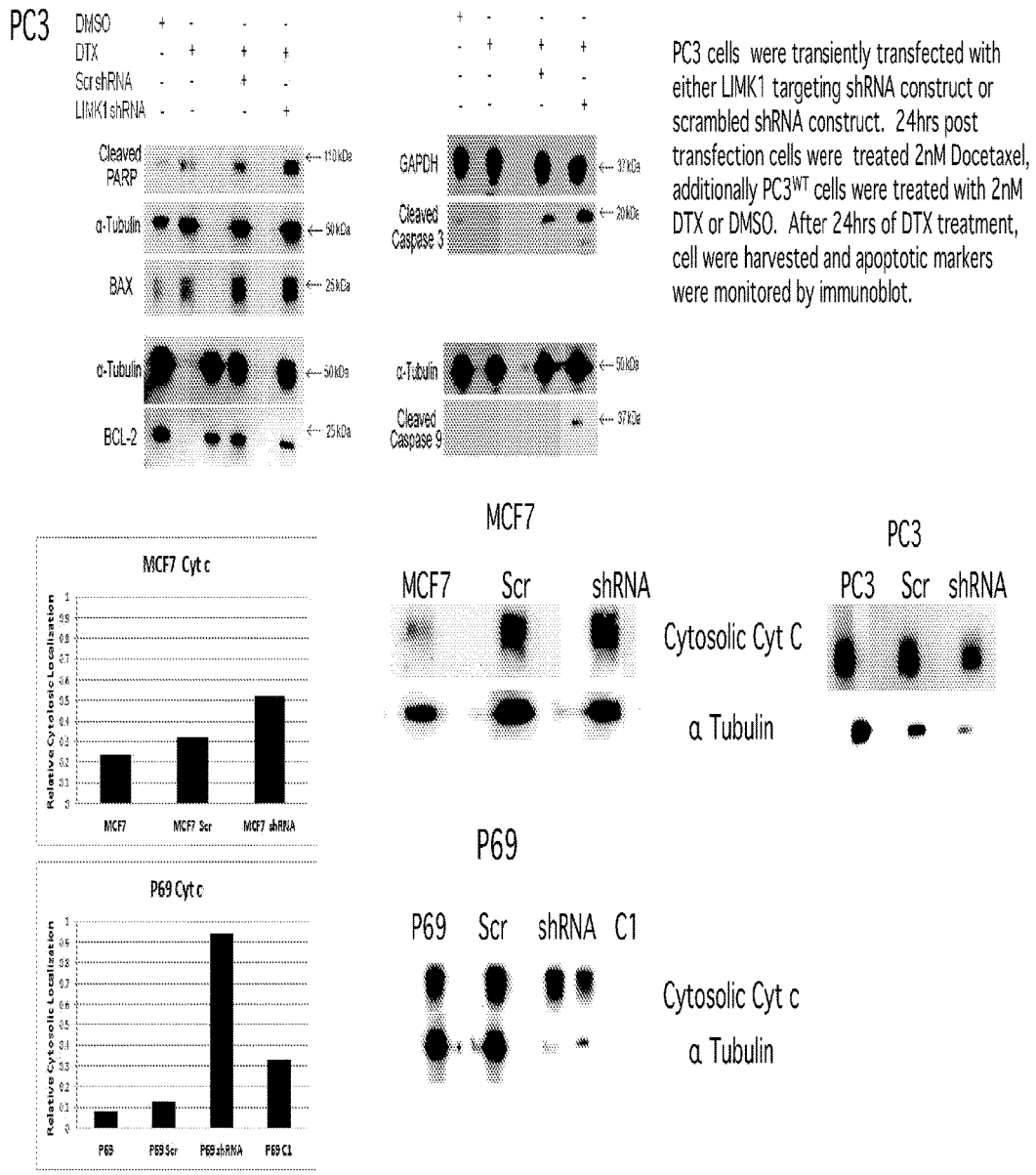

Cyt c Release: PC3 and MCF7 were transiently transfected with LIMK1 and Scrambled shRNA constructs, P69 cells were transiently transfected with LIMK1 expression vector, LIMK1-shRNA vector or control vector. 24hrs post transfection cells were treated with 2nM Docetaxel for 24hrs. Following treatment cells were harvested and cytosolic, mitochondrial, and nuclear fractions were isolated. Presence of Cyt c in the cytosol was monitored by immunoblot of cytosolic fraction. Densinometry was used to determine relative values.

Fig. 5

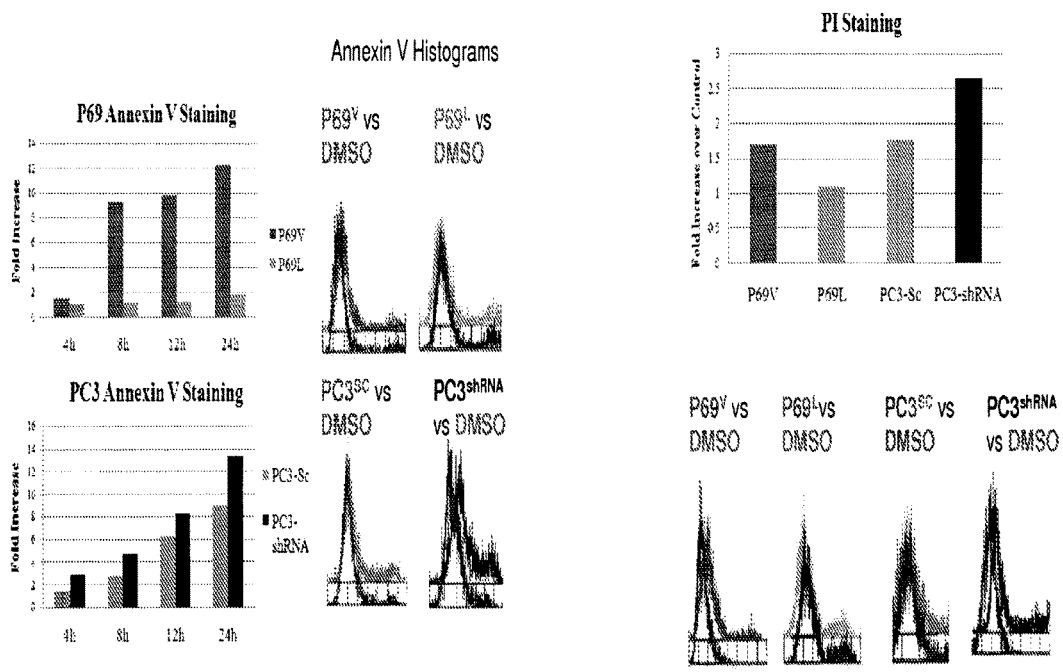

PC3 and MCF7 were transiently transfected with LIMK1 and Scrambled shRNA constructs, P69 cells were transiently transfected with LIMK1 expression vector or control vector. 24hrs post transfection cells were treated with 2nM Docetaxel for 4,8,12,and 24hrs. Early apoptotic events were monitored by Flow Cytometry of Annexin V stained cells. Graphs represent a fold difference in annexin V staining between Taxane and DMSO treatments. Late apoptotic events were monitored by propidium idiode staining. Cells were transfected as described above, and treated as above for 24hrs. Following treatment cells were washed and stained with PI (NO fixation or permeabilization).

Fig. 6

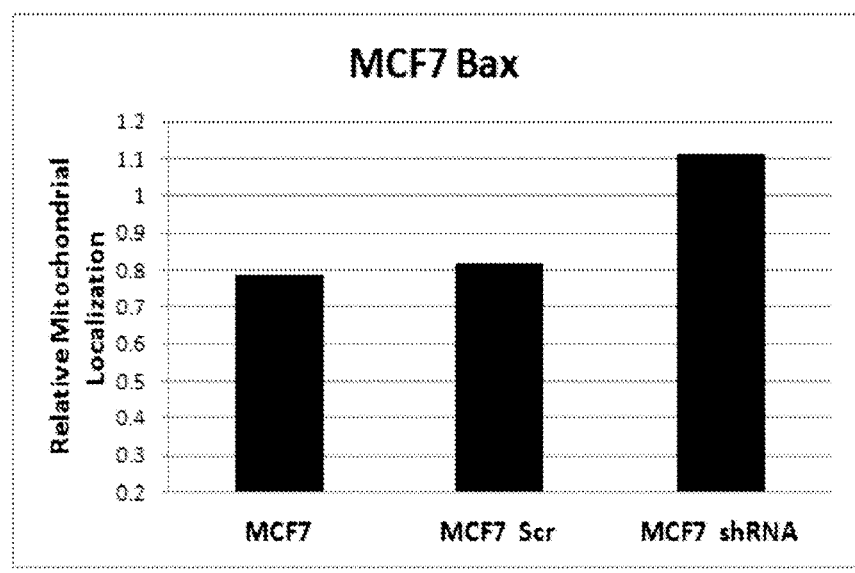
FIG. 7
Mitochondrial localized Bax
Prohibitin
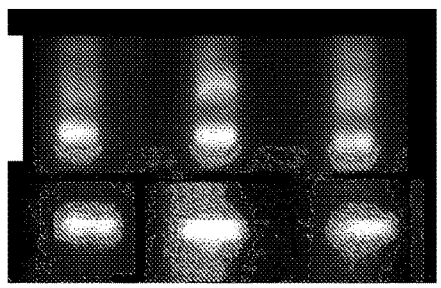

FIG. 7 cont.
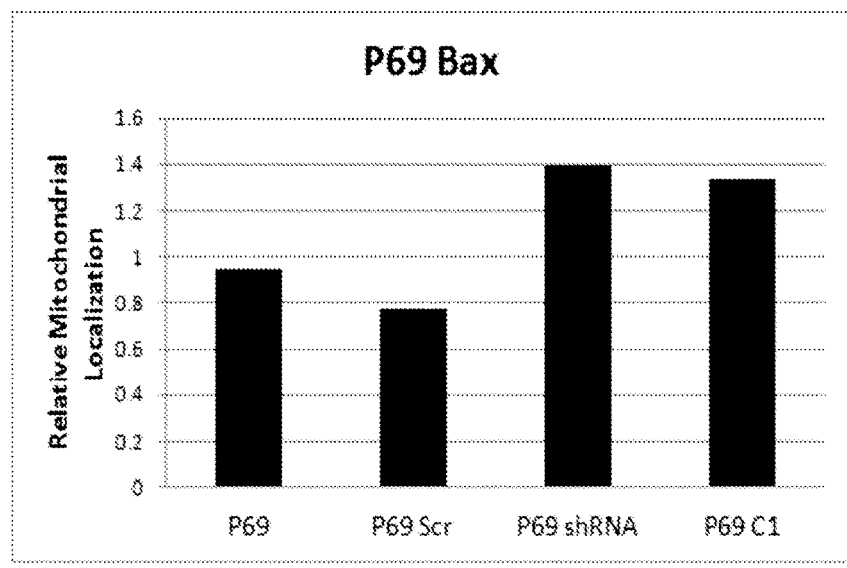
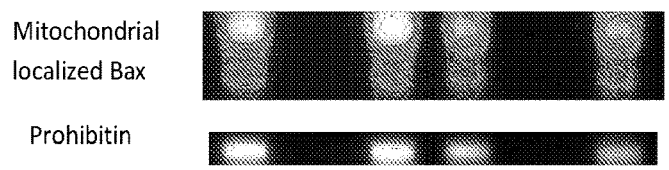
Mitochondrial localized Bax
Prohibitin
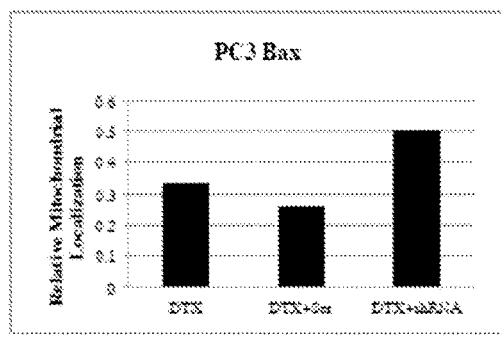
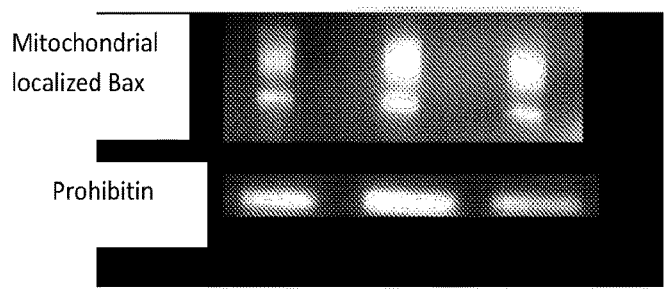
Mitochondrial localized Bax
Prohibitin

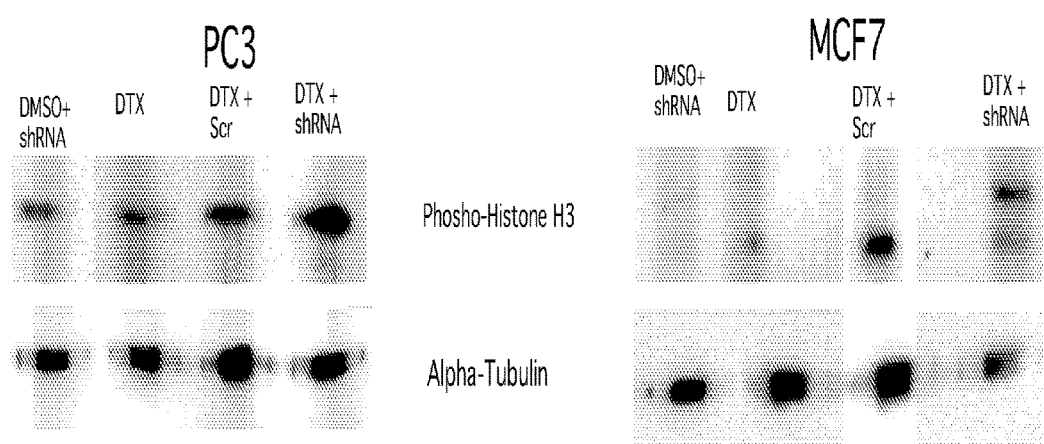

Phosphohistone staining: PC3 and MCF7 were transiently transfected with LIMK1 and Scrambled shRNA constructs and LIMK1-shRNA vector. 24hrs post transfection cells were treated with 2nM Docetaxel for 24hrs. Following treatment cells were harvested and total extracts were prepared. Phosphohistone concentration was analyzed in cell extracts to monitor mitotic arrest through activation of checkpoints. Data shows increased phosphohistone levels following inhibition of LIMK1 expression.

Fig. 8

INCREASING TAXANE SENSITIVITY IN CANCER CELLS

BACKGROUND

Despite recent advances in development of improved cancer therapeutics one of the many clinical challenges is that patients often show resistance to cancer drugs. This invention provides evidence that an alternate method of treatment of cancer could be adopted for improved efficacy of existing therapies and/or treatment of drug resistant cancers. Taxane compounds, such as docetaxel and paclitaxel, are microtubule-targeted tubulin-polymerizing agents and have proved to be the first line treatment choice for castration-resistant prostate cancer and tamoxifen-resistant breast cancer cells. However resistance to taxane compounds develops commonly due to altered beta tubulin isotypes or development of multidrug resistance (MDR) through activation of p-glycoprotein drug efflux pump. In addition there are serious side effects and systematic toxicity encountered with docetaxel treatment.

BRIEF DESCRIPTION OF THE DRAWINGS

FIG. 3: A) Western Blots: PC3 and MCF7 cells were transiently transfected with either LIMK1 targeting shRNA construct or Scrambled shRNA construct, 72 hrs after transfection cells were harvested and LIMK1 expression was monitored by immunoblot. P69 cells were transiently transfected with either LIMK1 expression vector or control vector, 48 hrs after transfection cells were harvested and LIMK1 expression was monitored by immunoblot. B) Cell Viability Assays: Cell lines were transiently transfected with their respective expression vectors. 24 hrs Post transfection, cell were treated with either Docetaxel (1 nM, 2 nM, or 5 nM), Paclitaxel (10 nM, 25 nM, 50 nM), or DMSO (highest comparable concentration) for 24 hrs, 48 hrs, and 72 hrs. Cell viability was then assessed by MTS assay and the viable population of control samples (control vector transfected and taxane treated) were normalized to 100%. Taxane treated samples were then graphed as a percentage of treated control.

FIG. 5: Higher LIMK1 expression diminished Taxane induced apoptotic response. PC3 cells were transiently transfected with either LIMK1 targeting shRNA construct or scrambled shRNA construct. 24 hrs post transfection cells were treated 2 nM Docetaxel, additionally PC3$^{WT}$ cells were treated with 2 nM DTX or DMSO. After 24 hrs of DTX treatment, cell were harvested and apoptotic markers were monitored by immunoblot. Cyt c Release: PC3 and MCF7 were transiently transfected with LIMK1 and Scrambled shRNA constructs, P69 cells were transiently transfected with LIMK1 expression vector, LIMK1-shRNA vector or control vector. 24 hrs post transfection cells were treated with 2 nM Docetaxel for 24 hrs. Following treatment cells were harvested and cytosolic, mitochondrial, and nuclear fractions were isolated. Presence of Cyt c in the cytosol was monitored by immunoblot of cytosolic fraction. Densinometry was used to determine relative values.

FIG. 6: PC3 and MCF7 were transiently transfected with LIMK1 and Scrambled shRNA constructs, P69 cells were transiently transfected with LIMK1 expression vector or control vector. 24 hrs post transfection cells were treated with 2 nM Docetaxel for 4, 8, 12, and 24 hrs. Early apoptotic events were monitored by Flow Cytometry of Annexin V stained cells. Graphs represent a fold difference in annexin V staining between Taxane and DMSO treatments. Late apoptotic events were monitored by propidium idiode staining. Cells were transfected as described above, and treated as above for 24 hrs. Following treatment cells were washed and stained with PI (NO fixation or permeabilization).

FIG. 7: Loss of LIMK1 expression increased mitochondrial translocation of Bax. Bax Translocation: PC3 and MCF7 were transiently transfected with LIMK1 and Scrambled shRNA constructs, P69 cells were transiently transfected with LIMK1 expression vector, LIMK1-shRNA vector or control vector. 24 hrs post transfection cells were treated with 2 nM Docetaxel for 24 hrs. Following treatment cells were harvested and cytosolic, mitochondrial, and nuclear fractions were isolated. Bax translocation to the mitochondria was monitored by immunoblot of the mitochondrial fraction. Densinometry was used to determine relative values.

FIG. 8: Phosphohistone staining: PC3 and MCF7 were transiently transfected with LIMK1 and Scrambled shRNA constructs and LIMK1-shRNA vector. 24hrs post transfection cells were treated with 2nM Docetaxel for 24hrs. Following treatment cells were harvested and total extracts were prepared. Phosphohistone concentration was analyzed in cell extracts to monitor mitotic arrest through activation of checkpoints. Data shows increased phosphohistone levels following inhibition of LIMK1 expression.

DETAILED DESCRIPTION

Figure 1:
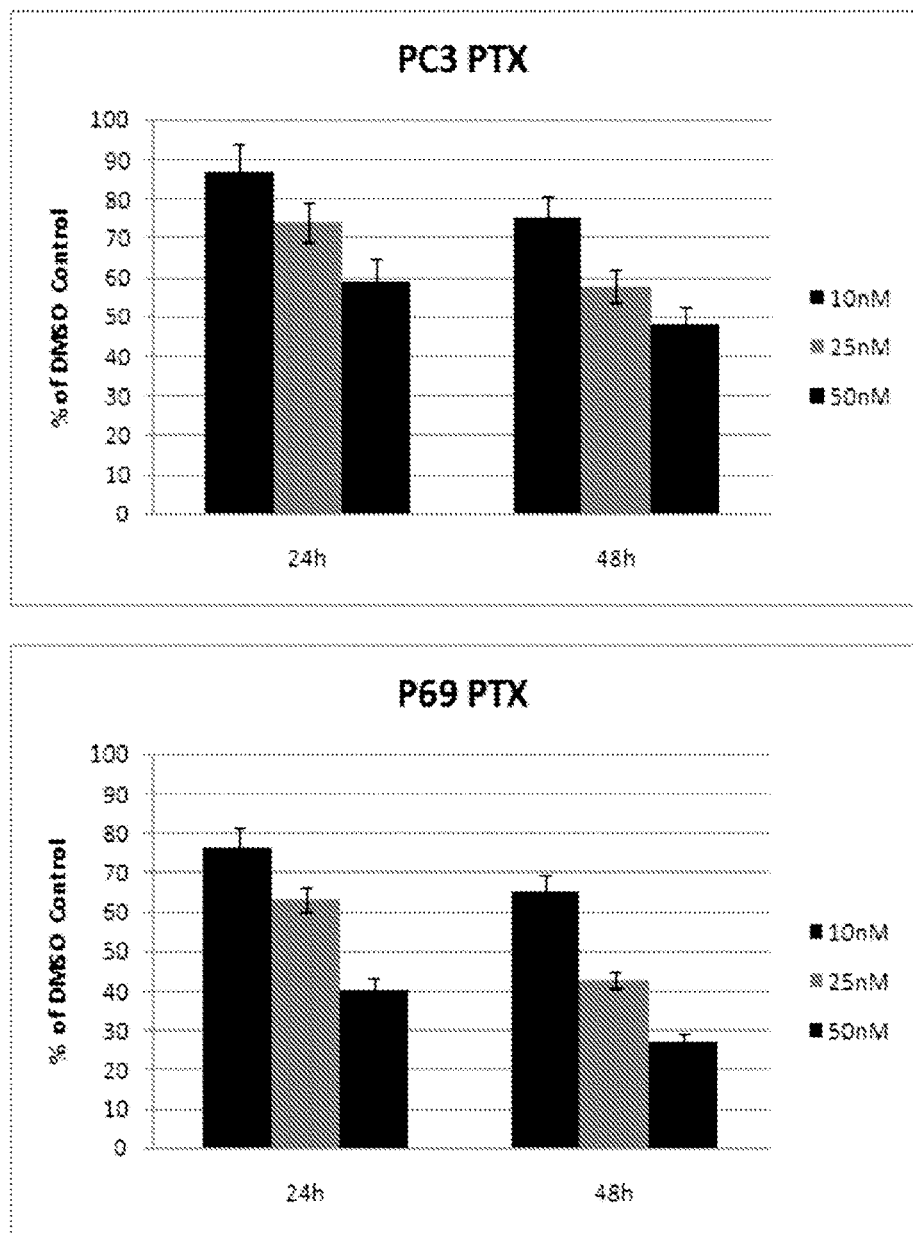
FIG. 1 A) Western Blots: Endogenous LIMK1 expression was monitored by immunoblotting whole cell lysates. B) Cell Viability Assays: Cell lines were treated with Docetaxel (1nM, 2nM, or 5nM) or DMSO (highest comparable concentration) for 24 hrs and 48 hrs. Cell viability was then assessed by MTS assay and viable cell populations following DMSO treatment were normalized to 100%. Taxane treated samples were then graphed as a percentage of DMSO. C) Cell Viability Assays: Cell lines were treated with Paclitaxel (10nM, 25nM, 50nM) or DMSO (highest comparable concentration) for 24 hrs and 48 hrs. Cell viability was then assessed by MTS assay and viable cell populations following DMSO treatment were normalized to 100%. Taxane treated samples were then graphed as a percentage of DMSO.

There is a need to enhance the efficacy of the taxane compounds by identifying novel targets, inhibition of which would induce mitotic arrest and apoptosis.

Disclosed herein are inventive embodiments that are based on the discovery that inhibition of LIM kinase 1 (LIMK1) in conjunction with taxane therapy potentiates the sensitivity of cells to the taxane therapy. Moreover, administration of an taxane therapy together with LIMK1 inhibition will enable the use of lesser amounts of individual inhibitor while obtaining the same effect. Further, this will minimize the side effects of individual drugs and delay the process of development of drug-resistant cancers.

Accordingly, in certain embodiments, disclosed herein relate to A) combination therapy of taxane(s) and LIMK1 inhibitors will improve effectiveness of taxanes and B) inhibitors of LIMK1 function may be used for patients showing resistance to taxane(s). The taxane and LIMK1 inhibitor are administered according to doses that ameliorate the side effects of taxane. In a specific embodiment, the taxane is provided in a composition that comprises less than 0.3 to 1.2 mg/ml taxane. More specifically, the composition may comprise less than 0.3 mg/ml taxane.

In one embodiment, a single interfering RNA targeting LIMK1 mRNA is administered to increase sensitivity to taxane therapy. In other embodiments, interfering RNA targeting LIMK1 and taxane therapy are administered to a subject sequentially or concurrently, thereby treating a targeted cancer.

RNA interference (RNAi) is a process by which double-stranded RNA (dsRNA) is used to silence gene expression. While not wanting to be bound by theory, RNAi begins with the cleavage of longer dsRNAs into small interfering RNAs (siRNAs) by an RNaseIII-like enzyme, dicer. SiRNAs are dsRNAs that are usually about 19 to 28 nucleotides, or 20 to 25 nucleotides, or 21 to 22 nucleotides in length and often contain 2-nucleotide 3' overhangs, and 5' phosphate and 3' hydroxyl termini. One strand of the siRNA is incorporated into a ribonucleoprotein complex known as the RNA-induced silencing complex (RISC). RISC uses this siRNA strand to identify mRNA molecules that are at least partially complementary to the incorporated siRNA strand, and then cleaves these target mRNAs or inhibits their translation. Therefore, the siRNA strand that is incorporated into RISC is known as the guide strand or the antisense strand. The other siRNA strand, known as the passenger strand or the sense strand, is eliminated from the siRNA and is at least partially homologous to the target mRNA. Those of skill in the art will recognize that, in principle, either strand of an siRNA can be incorporated into RISC and function as a guide strand. However, siRNA design (e.g., decreased siRNA duplex stability at the 5' end of the desired guide strand) can favor incorporation of the desired guide strand into RISC.

The antisense strand of an siRNA is the active guiding agent of the siRNA in that the antisense strand is incorporated into RISC, thus allowing RISC to identify target mRNAs with at least partial complementarity to the antisense siRNA strand for cleavage or translational repression. RISC-related cleavage of mRNAs having a sequence at least partially complementary to the guide strand leads to a decrease in the steady state level of that mRNA and of the corresponding protein encoded by this mRNA. Alternatively, RISC can also decrease expression of the corresponding protein via translational repression without cleavage of the target mRNA.

The GenBank database provides the DNA sequence for LIMK1 as accession no. NM_002314. Equivalents of the above cited LIMK1 mRNA sequence are alternative splice forms, allelic forms, isozymes, or a cognate thereof. A cognate is a LIMK1 mRNA from another mammalian species that is homologous to the cited human form (i.e., an ortholog).

The term "siRNA" as used herein refers to a double-stranded interfering RNA unless otherwise noted. Typically, an siRNA of the invention is a double-stranded nucleic acid molecule comprising two nucleotide strands, each strand having about 19 to about 28 nucleotides (i.e. about 19, 20, 21, 22, 23, 24, 25, 26, 27, or 28 nucleotides). The phrase "interfering RNA having a length of 19 to 49 nucleotides" when referring to a double-stranded interfering RNA means that the antisense and sense strands independently have a length of about 19 to about 49 nucleotides, including interfering RNA molecules where the sense and antisense strands are connected by a linker molecule.

In addition to siRNA molecules, other interfering RNA molecules and RNA-like molecules can interact with RISC and silence gene expression. Examples of other interfering RNA molecules that can interact with RISC include short hairpin RNAs (shRNAs), single-stranded siRNAs, microRNAs (miRNAs), and dicer-substrate 27-mer duplexes. Examples of RNA-like molecules that can interact with RISC include siRNA, single-stranded siRNA, microRNA, and shRNA molecules containing one or more chemically modified nucleotides, one or more non-nucleotides, one or more deoxyribonucleotides, and/or one or more non-phosphodiester linkages. All RNA or RNA-like molecules that can interact with RISC and participate in RISC-related changes in gene expression are referred to herein as "interfering RNAs" or "interfering RNA molecules." SiRNAs, single-stranded siRNAs, shRNAs, miRNAs, and dicer-substrate 27-mer duplexes are, therefore, subsets of "interfering RNAs" or "interfering RNA molecules."

Single-stranded interfering RNA has been found to effect mRNA silencing, albeit less efficiently than double-stranded RNA. Therefore, embodiments of the present invention also provide for administration of a single-stranded interfering RNA that has a region of at least near-perfect contiguous complementarity with a portion of the LIMK1 mRNA. The single-stranded interfering RNA has a length of about 19 to about 49 nucleotides as for the double-stranded interfering RNA cited above. The single-stranded interfering RNA has a 5' phosphate or is phosphorylated in situ or in vivo at the 5' position. The term "5' phosphorylated" is used to describe, for example, polynucleotides or oligonucleotides having a phosphate group attached via ester linkage to the C5 hydroxyl of the sugar (e.g., ribose, deoxyribose, or an analog of same) at the 5' end of the polynucleotide or oligonucleotide.

Single-stranded interfering RNAs can be synthesized chemically or by in vitro transcription or expressed endogenously from vectors or expression cassettes as described herein in reference to double-stranded interfering RNAs. 5' Phosphate groups may be added via a kinase, or a 5' phosphate may be the result of nuclease cleavage of an RNA. A hairpin interfering RNA is a single molecule (e.g., a single oligonucleotide chain) that comprises both the sense and antisense strands of an interfering RNA in a stem-loop or hairpin structure (e.g., a shRNA). For example, shRNAs can be expressed from DNA vectors in which the DNA oligonucleotides encoding a sense interfering RNA strand are linked to the DNA oligonucleotides encoding the reverse complementary antisense interfering RNA strand by a short spacer. If needed for the chosen expression vector, 3' terminal T's and nucleotides forming restriction sites may be added. The resulting RNA transcript folds back onto itself to form a stem-loop structure.

Nucleic acid sequences cited herein are written in a 5' to 3' direction unless indicated otherwise. The term "nucleic acid," as used herein, refers to either DNA or RNA or a modified form thereof comprising the purine or pyrimidine bases present in DNA (adenine "A," cytosine "C," guanine "G," thymine "T") or in RNA (adenine "A," cytosine "C," guanine "G," uracil "U"). Interfering RNAs provided herein may comprise "T" bases, particularly at 3' ends, even though "T" bases do not naturally occur in RNA. "Nucleic acid" includes the terms "oligonucleotide" and "polynucleotide" and can refer to a single-stranded molecule or a double-stranded molecule. A double-stranded molecule is formed by Watson-Crick base pairing between A and T bases, C and G bases, and between A and U bases. The strands of a double-stranded molecule may have partial, substantial or full complementarity to each other and will form a duplex hybrid, the strength of bonding of which is dependent upon the nature and degree of complementarity of the sequence of bases.

In certain embodiments, interfering RNA target sequences (e.g., siRNA target sequences) within a target mRNA sequence are selected using available design tools. Interfering RNAs corresponding to a LIMK1 target sequence are then tested in vitro by transfection of cells expressing the target mRNA followed by assessment of knockdown as described herein. The interfering RNAs can be further evaluated in vivo using animal models as described herein.

Techniques for selecting target sequences for siRNAs are provided, for example, by Tuschl, T. et al., "The siRNA User Guide," revised May 6, 2004, available on the Rockefeller University web site; by Technical Bulletin #506, "siRNA Design Guidelines," Ambion Inc. at Ambion's web site; and by other web-based design tools at, for example, the Invitrogen, Dharmacon, Integrated DNA Technologies, Genscript, or Proligo web sites. Initial search parameters can include G/C contents between 35% and 55% and siRNA lengths between 19 and 27 nucleotides. The target sequence may be located in the coding region or in the 5' or 3' untranslated regions of the mRNA. The target sequences can be used to derive interfering RNA molecules, such as those described herein.

In certain embodiments, silencing of human LIMK1 genes should be based on the sequences found at NM_002314 (SEQ ID NO. 1) version NM_002314.2 (GI: 8051616) and NP_002305 (SEQ ID NO. 2) version NP_002305.1 (GI:4505001). In a particular embodiment, siRNA disclosed by Gorovoy et al., *MolVis* 2008 14:1951-9 is implemented. The teachings of this and any other reference cited herein is incorporated in its entirety to the extent not inconsistent with the teachings herein.

In a specific embodiment, the interfering RNA molecule targeting LIMK1 targets AAGGACAAGAGGCTCAACT-TCATCACTGA (SEQ ID NO. 1)

As used herein, the term "effective amount" refers to the amount of a therapy that is sufficient to result in the prevention of the development, recurrence, or onset of cancer and one or more symptoms thereof, to enhance or improve the prophylactic effect(s) of another therapy, reduce the severity, the duration of cancer, ameliorate one or more symptoms of cancer, prevent the advancement of cancer, cause regression of cancer, and/or enhance or improve the therapeutic effect(s) of another therapy. In an embodiment of the invention, the amount of a therapy is effective to achieve one, two, three or more of the following results following the administration of one, two, three or more therapies: (1) a stabilization, reduction or elimination of the cancer stem cell population; (2) a stabilization, reduction or elimination in the cancer cell population; (3) a stabilization or reduction in the growth of a tumor or neoplasm; (4) an impairment in the formation of a tumor; (5) eradication, removal, or control of primary, regional and/or metastatic cancer; (6) a reduction in mortality; (7) an increase in disease-free, relapse-free, progression-free, and/or overall survival, duration, or rate; (8) an increase in the response rate, the durability of response, or number of patients who respond or are in remission; (9) a decrease in hospitalization rate; (10) a decrease in hospitalization lengths; (11) the size of the tumor is maintained and does not increase or increases by less than 10%, preferably less than 5%, preferably less than 4%, preferably less than 2%; (12) an increase in the number of patients in remission; (13) an increase in the length or duration of remission; (14) a decrease in the recurrence rate of cancer; (15) an increase in the time to recurrence of cancer; and (16) an amelioration of cancer-related symptoms and/or quality of life. Alternatively, the term "effective amount" refers to an amount resulting in a decrease in LIMK1 activity in a cancer cell treated with a LIMK1 inhibitor relative to a cancer cell not treated with LIMK1 inhibitor.

As used herein, the terms "subject" and "patient" are used interchangeably. As used herein, the term "subject" refers to an animal, preferably a mammal such as a non-primate (e.g., cows, pigs, horses, cats, dogs, rats etc.) and a primate (e.g., monkey and human), and most preferably a human. In some embodiments, the subject is a non-human animal such as a farm animal (e.g., a horse, pig, or cow) or a pet (e.g., a dog or cat). In a specific embodiment, the subject is an elderly human. In another embodiment, the subject is a human adult. In another embodiment, the subject is a human child. In yet another embodiment, the subject is a human infant.

As used herein, the term "chemotherapeutic agent" refers to any molecule, compound, and/or substance that is used for the purpose of treating and/or managing cancer. Examples of therapeutic agents include, but are not limited to, proteins, immunoglobulins (e.g., multi-specific Igs, single chain Igs, Ig fragments, polyclonal antibodies and their fragments, monoclonal antibodies and their fragments), antibody conjugates or antibody fragment conjugates, peptides (e.g., peptide receptors, selectins), binding proteins, chemospecific agents, chemotoxic agents (e.g., anti-cancer agents), radiation, chemotherapy, antiangiogenic agents, and small molecule drugs. Therapeutic agents may be a(n) anti-angiogenesis therapy, targeted therapy, radioimmunotherapy, small molecule therapy, biologic therapy, epigenetic therapy, toxin therapy, differentiation therapy, pro-drug activating enzyme therapy, antibody therapy, chemotherapy, radiation therapy, hormonal therapy, immunotherapy, or protein therapy.

As used herein, the terms "therapies" and "therapy" can refer to any method(s), composition(s), and/or agent(s) that can be used in the treatment of a cancer or one or more symptoms thereof. In certain embodiments, the terms "therapy" and "therapies" refer to chemotherapy, radiation therapy, radioimmunotherapy, hormonal therapy, targeted therapy, toxin therapy, pro-drug activating enzyme therapy, protein therapy, antibody therapy, small molecule therapy, epigenetic therapy, demethylation therapy, histone deacetylase inhibitor therapy, differentiation therapy, antiangiogenic therapy, biological therapy including immunotherapy and/or other therapies useful in the treatment of a cancer or one or more symptoms thereof.

As used herein, the term "taxane" refers to any known taxane compound, or known taxane derivatives, or salts thereof. Two classic taxane compounds widely used as chemotherapeutic agents are paclitaxel and docetaxel. These compounds and derivatives thereof, are well-known in the art, and are disclosed for example in the following references: U.S. Pat. Nos. 5,912,263, 6,136,808, 6,939,978, 5,693,666, 6,538,020, 6,509,370, 7,060,724, 6,569,459, 6,680,877, 6,541,508, 6,649,777, 5,998,656, 6,028,005, 5,994,576, and 6,147,234. These patents are cited and incorporated by reference for taxanes, taxane derivatives, taxane containing compositions, and modes of administration that can be used in accordance with taxane therapy as described herein.

The term "taxane therapy" refers to the provision of a taxane to a subject.

As used herein, the terms "treat", "treatment", and "treating" in the context of the administration of a therapy to a subject refer to the reduction or inhibition of the progression and/or duration of cancer, the reduction or amelioration of the severity of cancer, and/or the amelioration of one or more symptoms thereof resulting from the administration of one or more therapies. In specific embodiments, such terms refer to one, two, or three or more results following the administration of one, two, three or more therapies: (1) a stabilization, reduction or elimination of the cancer stem cell population; (2) a stabilization, reduction or elimination in the cancer cell population; (3) a stabilization or reduction in the growth of a tumor or neoplasm; (4) an impairment in the formation of a tumor; (5) eradication, removal, or control of primary, regional and/or metastatic cancer; (6) a reduction in mortality; (7) an increase in disease-free, relapse-free, progression-free, and/or overall survival, duration, or rate; (8) an increase in the response rate, the durability of response, or number of patients who respond or are in remission; (9) a decrease in hospitalization rate; (10) a decrease in hospitalization lengths; (11) the size of the tumor is maintained and does not increase or increases by less than 10%, preferably less than 5%, preferably less than 4%, preferably less than 2%; (12) an increase in the number of patients in remission; (13) an increase in the length or duration of remission; (14) a decrease in the recurrence rate of cancer; (15) an increase in the time to recurrence of cancer; and (16) an amelioration of cancer-related symptoms and/or quality of life. In certain embodiments, such terms refer to a stabilization or reduction in the cancer stem cell population. In some embodiments, such terms refer to a stabilization or reduction in the growth of cancer cells. In some embodiments, such terms refer to a stabilization or reduction in the cancer stem cell population and a reduction in the cancer cell population. In some embodiments, such terms refer to a stabilization or reduction in the growth and/or formation of a tumor. In some embodiments, such terms refer to the eradication, removal, or control of primary, regional, or metastatic cancer (e.g., the minimization or delay of the spread of cancer). In some embodiments, such terms refer to a reduction in mortality and/or an increase in survival rate of a patient population. In further embodiments, such terms refer to an increase in the response rate, the durability of response, or number of patients who respond or are in remission. In some embodiments, such terms refer to a decrease in hospitalization rate of a patient population and/or a decrease in hospitalization length for a patient population.

The present invention also provides methods for treating cancer, the methods comprising administering to a patient (e.g., a human patient) in need thereof, a therapeutically effective regimen, the regimen comprising administering to the patient a taxane therapy and co-administering an inhibitor of LIMK1, and optionally one or more additional therapies, said additional therapy having mechanism of action apart from that exhibited by taxanes and LIMK1 inhibitors. The compound of the invention and the additional therapy can be administered separately, concurrently, or sequentially. The combination of agents can act additively or synergistically. PCT/US10/35800; filed May 21, 2010 is cited herein in its entirety, and specifically for a teaching of the many additional therapies that may be administered in conjunction with LIMK1 inhibitors. Macdonald et al. Mol Cancer Ther, 7:3490 (2008) is cited for teaching of LIMK1 inhibitors and methodology for indentifying such inhibitors, and U.S. application Ser. No. 12/706,218 is cited for teachings of LIMK1 inhibitors. In a specific embodiment, the LIMK1 inhibitor is BMS-5:

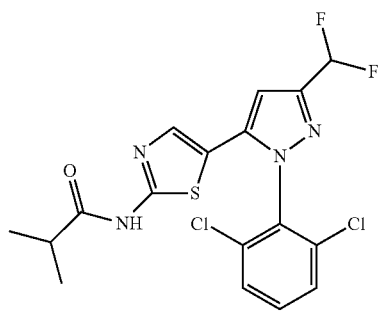 [SMILES: CC(C)C(=O)Nc1ncc(-c2cc(C(F)F)nn2-c2c(Cl)cccc2Cl)s1]

In general, the taxane, LIMK1 inhibitor and/or an additional therapy, will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 1000 mg, conveniently administered, e.g. in divided doses up to four times a day or in retard form. Suitable unit dosage forms for oral administration comprise from ca. 1 to 1000 mg active ingredient. In view of the inventor's discovery that taxane(s) and LIMK1 inhibitors can work together synergistically to treat taxane resistant cancer cells, this will allow dosages of each to be administered at lower levels than that required for usage of only one or the other classes of inhibitors. Synergy refers to the additive effect of using a dose of another inhibitor that is not achieved by using the same dose of the same inhibitor. This is believed to lessen the possible toxicity that may be experienced with higher doses of a certain chemotherapeutic agent. For example, if 100 mg is a determined daily dosage for only a taxane, then only 45 mg daily dosage of the taxane may be needed when 45-50 mg of a LIMK1 inhibitor is administered in combination to achieve the same treatment effect.

Pharmaceutical compositions of the invention can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

In addition to the active ingredients, these pharmaceutical compositions can contain suitable pharmaceutically acceptable carriers comprising excipients and auxiliaries which facilitate processing of the active compounds into preparations which can be used pharmaceutically.

Pharmaceutical compositions comprising a compound of the present invention in free form or in a pharmaceutically acceptable salt form in association with at least one pharmaceutically acceptable carrier or diluent may be manufactured in a conventional manner by mixing, granulating or coating methods. For example, oral compositions may be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets, together with c) binders, e.g., magnesium aluminum silicate, starch paste, gelatin, tragacanth, methylcellulose, sodium carboxymethylcellulose and/or polyvinylpyrrolidone; and if desired, d) disintegrants, e.g., starches, agar, alginic acid or its sodium salt, or effervescent mixtures; and/or e) absorbents, colorants, flavors and sweeteners. Injectable compositions may be aqueous isotonic solutions or suspensions, and suppositories may be prepared from fatty emulsions or suspensions.

Further, the compounds (e.g. protein or delivery vehicle) for use in the method of the invention can be formulated in a sustained release preparation. For example, the compounds can be formulated with a suitable polymer or hydrophobic material which provides sustained and/or controlled release properties to the active agent compound. As such, the compounds for use the method of the invention can be administered in the form of microparticles for example, by injection or in the form of wafers or discs by implantation.

In accordance with the method of the invention, an expression vector is a viral or a non-viral expression vector. Viral expression vectors which may be used advantageously in the method of the invention include, but are not limited to, an adeno associated virus (AAV) vector, a lentivirus vector, an adenovirus vector, and a herpes simplex virus (HSV) vector.

In additional embodiments, the composition comprises sRNA or miRNA specific for LIMK1, an antisense nucleotide specific for LIMK1, and/or shRNA. In an alternative embodiment, the composition comprises an antibody specific to LIMK1.

In another embodiment, administering a therapeutically effective amount of a composition includes a composition comprising: a composition that inhibits the expression or action of LIMK1, and a pharmaceutically acceptable excipient.

In further embodiments, the composition includes an LIMK1 sRNA, an shRNA, an antibody specific to LIMK1, and/or an antisense nucleotide specific for LIMK1.

Many of the embodiments of the subject invention make reference to particular methods of inhibiting expression. The subject invention is not to be limited to any of the particular methods described. One such method includes sRNA (small interfering/short interfering/silencing RNA). SiRNA most often is involved in the RNA interference pathway where it interferes with the expression of a specific gene. In addition to its role in the RNA interference pathway, sRNA also act in RNA interference-related pathways, e.g., as an antiviral mechanism or in shaping the chromatin structure of a genome.

Another method by which to inhibit expression and to inhibit the expression of LIMK1 in particular is shRNA. ShRNA (short hairpin or small hairpin RNA) refers to a sequence of RNA that makes a tight hairpin turn and is used to silence gene expression via RNA interference. It uses a vector introduced into cells and a U6 or H1 promoter to ensure that the shRNA is always expressed. The shRNA hairpin structure is cleaved by cellular machinery into siRNA which is then bound to the RNA-induced silencing complex. This complex binds to and cleaves mRNAs which match the siRNA that is bound to it.

LIMK1 can also be blocked by subjecting procured cells to an antibody specific to LIMK1. An antisense nucleotide may also be used to block or inhibit expression, in particular, the expression of LIMK1. Expression may also be inhibited with the use of a morpholino oligomer or phosphorodiamidate morpholino oligomer (PMO). PMOs are an antisense technology used to block access of other molecules to specific sequences within nucleic acid. PMOs are often used as a research tool for reverse genetics, and function by knocking down gene function. This is achieved by preventing cells from making a targeted protein or by modifying splicing of pre-mRNA.

As used herein, the term "cancer" refers to a neoplasm or tumor resulting from abnormal uncontrolled growth of cells. The term "cancer" encompasses a disease involving both pre-malignant and malignant cancer cells. In some embodiments, cancer refers to a localized overgrowth of cells that has not spread to other parts of a subject, i.e., a benign tumor. In other embodiments, cancer refers to a malignant tumor, which has invaded and destroyed neighbouring body structures and spread to distant sites. In yet other embodiments, the cancer is associated with a specific cancer antigen.

In particular embodiments of this aspect, the cancer is fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiform, astrocytoma, medulloblastoma, craniopharyngioma, ependymoma, pinealoma, hemangioblastoma, acoustic neuroma, oligodendroglioma, meningioma, skin cancer, melanoma, neuroblastoma, or retinoblastoma.

As used herein, the term "cancer cells" refers to cells that acquire a characteristic set of functional capabilities during their development, including the ability to evade apoptosis, self-sufficiency in growth signals, insensitivity to anti-growth signals, tissue invasion/metastasis, significant growth potential, and/or sustained angiogenesis. The term "cancer cells" is meant to encompass both pre-malignant and malignant cancer cells. Specific examples of cancer cells are cells pertaining to those comprised within cancer as described above. The term "cancer cell" refers to at least one of a group of cancer cells.

EXAMPLES

LIMK1 Expression Correlates with Insensitivity to Taxane Compounds

To better understand the effect of LIMK1 expression on taxane sensitivity, cell lines expressing differing levels of LIMK1 were selected. Epithelial cell lines from both prostate and breast origin were screened for relative LIMK1 expression by Western blotting (Data not shown). From this preliminary screening, two prostate cell lines (P69 and PC-3) along with two breast cell lines (MDA-MB-231 and MCF7) cell lines were selected for further investigation. Both PC-3 and MCF7 expressed higher levels of LIMK1 compared to P69 and MDA-MB-231 (FIGS. 1A and B). Taxane sensitivity was initially assessed by determining cell viability following treatments with both Paclitaxel (PTX) and Docetaxel (DTX). The cell lines were treated with three concentrations of each taxane (DTX 1, 2, 5 nM) (PTX 10, 25, 50 nM) for 24 and 48 hrs. Following treatment, both P69 and MDA-MB-231 had a smaller population of viable cells compared to PC-3 and MCF7 (FIG. 10). From the data collected single concentrations of each taxane were chosen that exhibited cytotoxicity while allowing discernable differences in sensitivity between cell lines.

To confirm the results of the MTS assay, while further elucidating the link between LIMK1 expression and taxane sensitivity, the effects of taxane treatment on cell cycle were analyzed. Cells were treated with 2 µM docetaxel for 24 hrs then stained with propidium iodide. Using flow cytometry to monitor DNA content, the percentages of cells in each phase of the cell cycle including the percentage of cells in the sub-G1 population (FIGS. 2A and B) were determined. Following 12 hrs of docetaxel treatment, all cell lines showed varying enrichment of cells in G2. Although after 24 hrs of treatment, the difference between cells lines became more apparent. P69 displayed a prominent G2 peak, and had a sub-G1 population of 15%. This was contrasted by that of the PC-3 cell line which exhibited a profile very close to that of the DMSO treated control sample, and only had a sub-G1 population of 6%. The MCF7 cell line appeared to cycle through the G2 arrest similar to PC-3 and had a sub-G1 population of only 5%. Nearly half of the MDA-MB-231 cells had cycled back to G1 by 24 hrs of treatment, but it displayed the largest sub-G1 population at 25%.

Ectopic Expression of LIMK1 Correlates with Taxane Sensitivity:

In order to confirm the implication of LIMK1 induced resistance to taxane treatment, the expression of LIMK1 in each cell line was altered. PC-3 and MCF-7 were transiently transfected with LIMK1 shRNA constructs before being treated with both taxanes, and LIMK1 expression was monitored by western blotting (FIG. 3A). Sensitivity to the taxane treatment was monitored by MTS assay. We observed that after LIMK1 knockdown, both PC-3 and MCF-7 exhibited a smaller population of viable cells after taxane treatment at all concentrations, more importantly the lower concentrations exhibited the largest difference in the number of viable cells between knockdown and control shRNA (FIG. 3B). Additionally, cell cycle analysis by flow cytometry showed an increase in the sub-G1 population of the cells expressing the LIMK1 shRNA over the cells expressing the control shRNA.

To show the reciprocal affect of expression we transiently transfected a LIMK1 expression vector into MDA-MB-231 and repeated the same taxane treatments. Increased LIMK1 expression was monitored by western blotting (FIG. 3A) and cell viability was quantified by MTS assay. In contrast to LIMK1 knockdown in PC-3 and MCF-7, increased expression of LIMK1 in MDA-MB-231 cells resulted in more viable cells following taxane treatment compared against vector control.

The P69 cell line was chosen to both knock-down and knock-in LIMK1 because it is not malignant, and thus reduces the possible effects of additional variations in the cell. Western blotting showed the both the decrease and increase in LIMK1 expression following transient transfection with the LIMK1 shRNA construct and LIMK1 expression vector respectively (FIG. 3A). As with the previous cell lines MTS assays were performed following taxane treatment. P69 cells expressing the LIMK1 shRNA showed decreased cell viability (FIGS. 3B and C) while cells expressing the LIMK1 expression vector had more viable cells compared to control vector, the difference was not as significant as the knockdown. This disparity may be a consequence of the toxic effect of LIMK1 over-expression in a portion of the transfected population.

From the previous experiments, we found that cells expressing lower LIMK1 were less viable and had a larger sub-G1 population following taxane treatment compared to those cells expressing higher LIMK1 levels. It was desired to confirm that these results were from the induction of apoptosis and not a necrotic event. Analysis of western blots, using docetaxel treated cell lysates, showed increased levels of cleaved caspases 3, cleaved caspases 9 and cleaved PARP. In addition cells expressing LIMK1 shRNA had increased levels of cytosolic Cytochrome c compared to cells expressing scrambled shRNA.

To better understand the mechanism by which LIMK1 is subverting taxane induced apoptosis, the expression of LIMK1 was compared against those of the Bcl2 family.

Figure 2:
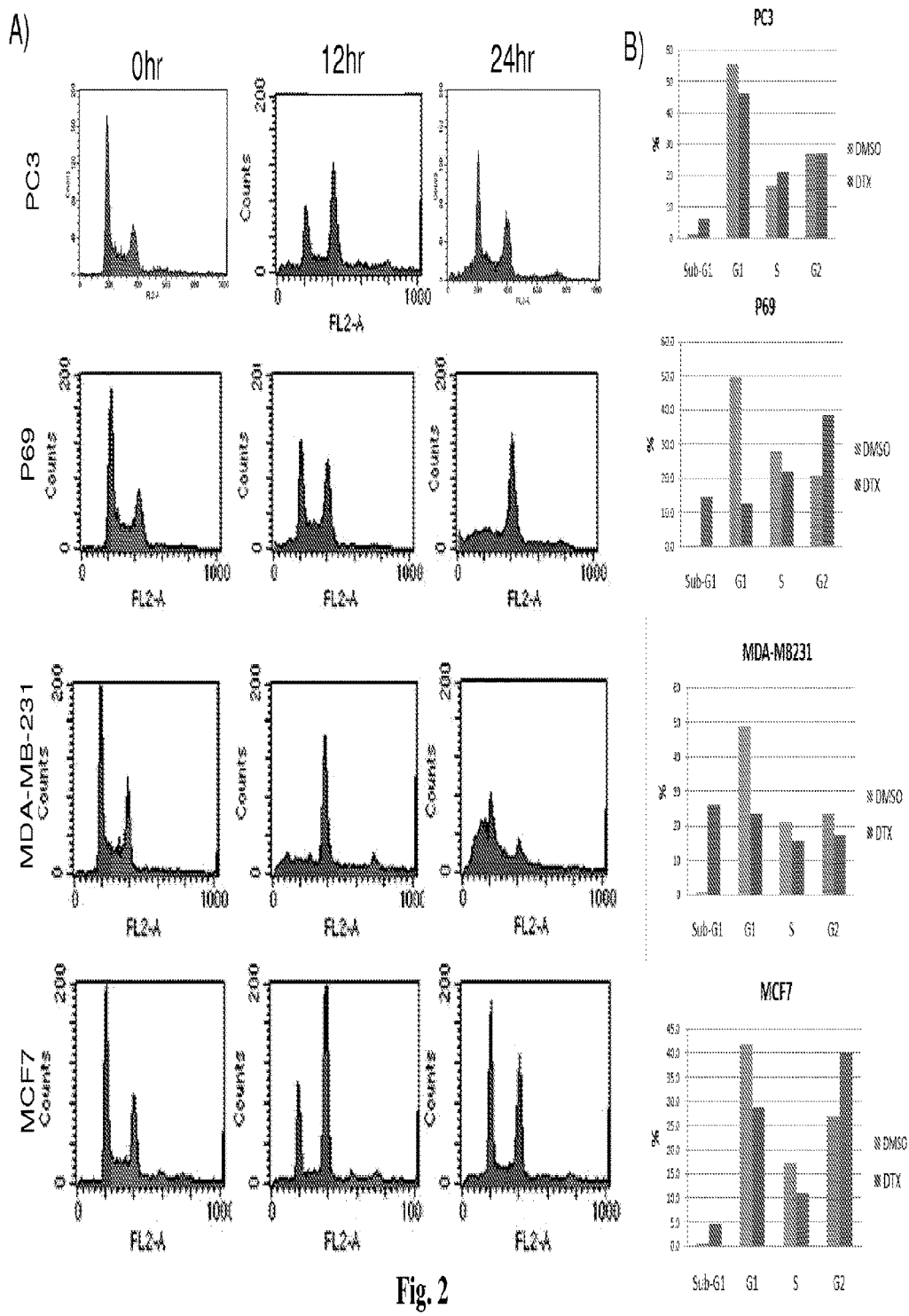
FIG. 2: LIMK1 Expression correlates with sensitivity to Taxane compounds. A) 2D Flow Cytometry: Cell lines were treated with 2 nM Docetaxel or DMSO for 12 hrs and 24 hrs. Following treatment cells were fixed, permeabilized, then stained with propidium iodide to monitor DNA content. B) Graphical analysis of average cell cycle populations following 24 hrs of 2 nM Docetaxel treatment, depicted as a percentage of total cell number.
Figure 4:
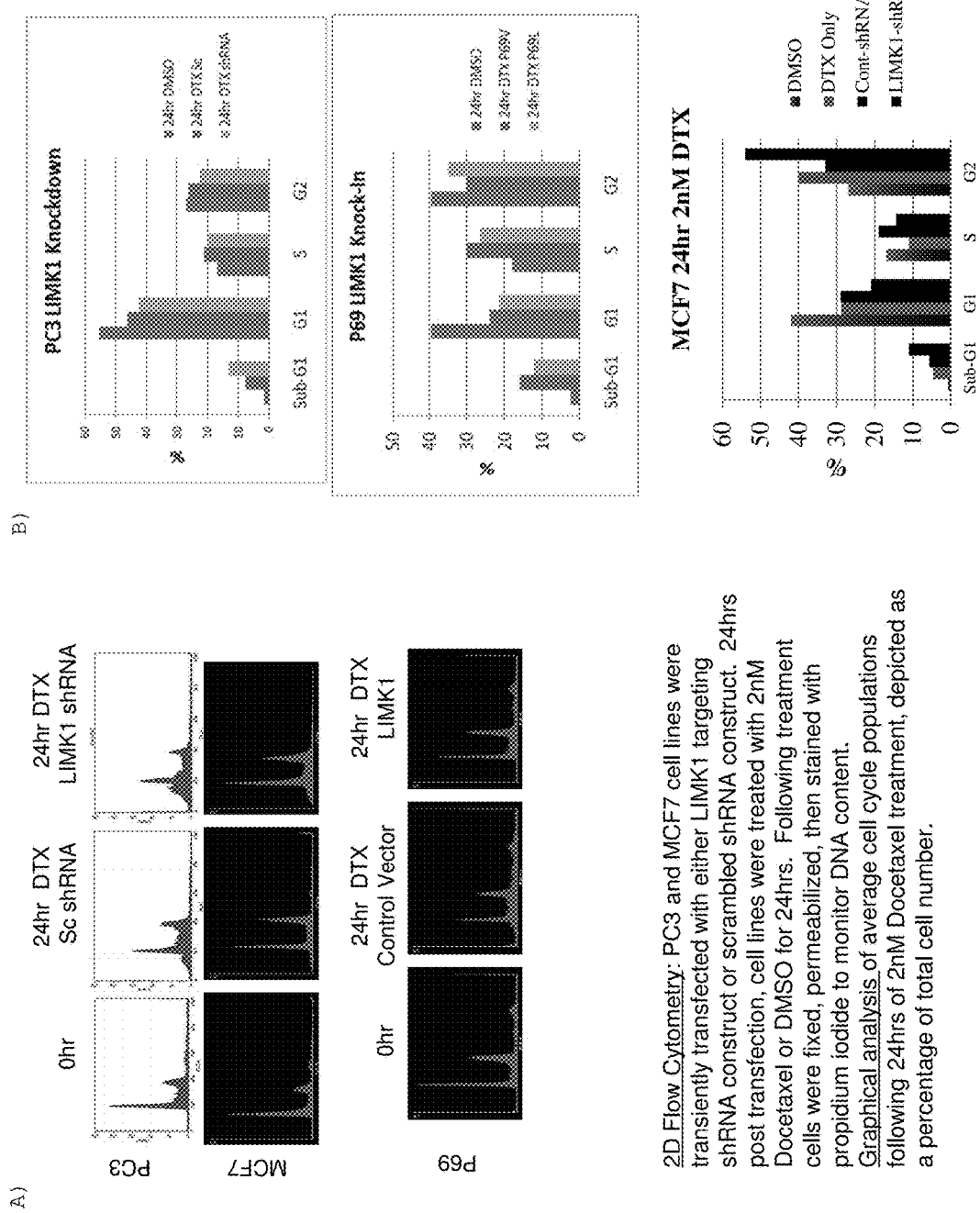
FIG. 4: A) 2D Flow Cytometry: PC3 and MCF7 cell lines were transiently transfected with either LIMK1 targeting shRNA construct or scrambled shRNA construct. 24 hrs post transfection, cell lines were treated with 2 nM Docetaxel or DMSO for 24 hrs. Following treatment cells were fixed, permeabilized, then stained with propidium iodide to monitor DNA content. B) Graphical analysis of average cell cycle populations following 24 hrs of 2 nM Docetaxel treatment, depicted as a percentage of total cell number.

The description of the data in FIGS. 1-8 is provided above. The following is a general summary of Data found in FIGS. 1-8 and the conclusions derived therefrom:

FIGS. 1 and 2 demonstrate that LIMK1 expression correlates with sensitivity to Taxane compounds. FIGS. 3 and 4 show that ectopic expression of LIMK1 increases Taxane resistance and that LIMK1 knockdown reduced Taxane resistance. FIGS. 5 and 6 demonstrate that higher LIMK1 expression diminished Taxane induced apoptotic response. FIG. 7 shows that loss of LIMK1 expression increased mitochondrial translocation of Bax. FIG. 8 shows that loss of LIMK1 expression increased phosphohistone concentration which indicates activation of mitotic checkpoint in response to DTX treatment which normally leads to mitotic arrest. It was observed that after LIMK1 knockdown, PC-3, P69 and MCF-7 cells all exhibited a smaller population of viable cells after taxane treatment at all concentrations. Interestingly, the lower concentrations exhibited the largest difference in the number of viable cells between knockdown and control shRNA.

Methods and Materials:

Cell Culture and Transfection.

PC-3 cells were maintained in F12 Ham (Sigma, St. Louis, Mo.) containing 10% FBS (Atlanta Biologicals, Lawrenceville, Ga.). MCF7 and MDA-MB-231 cells were maintained in DMEM (Invitrogen) containing 10% FBS (Atlanta Biologicals, Lawrenceville, Ga.). P69 cells were maintained in RPMI containing EGF (10 ng/ml), dexamethasone (0.1 µM), Gentamycin (50 µg/ml), ITS mix (Insulin 5 µg/ml, Transferrin 5 µl/ml, Selenium 5 ng/ml). Cells were transfected with Fugene HD or Extreme Gene HP (Roche, Basel, Switzerland).

Taxane Treatment.

Cells were treated with complete media containing docetaxel (Fluka) or paclitaxel (Sigma) dissolved in DMSO (Sigma).

Antibodies.

Western blots were probed with the following antibodies: mouse anti-human-GAPDH (Sigma); mouse anti-FLAG (Sigma); rabbit anti-human-LIMK1 (Santa Cruz; Santa Cruz, Calif.); mouse anti-human LIMK1 (BD Pharmingen, San Diego, Calif.); rabbit anti-Cleaved Caspase 3/9 and anti-Cleaved PARP (Cell Signaling); rabbit anti-human-alpha-tubulin (Sigma). Mouse anti-Cytochrome c (R&D Systems). Rabbit anti-Prohibitin (Abcam). Rabbit anti-Bax (Santa Cruz). Rabbit anti-Bcl2 (Cell Signaling)

Plasmid DNA and shRNA Constructs.

The LIMK1 coding sequence was cloned into the mammalian expression vector pCMV-3×FLAG resulting in pCMV-LIMK1-FLAG. The LIMK1 shRNA construct and control shRNA construct were described previously 48.

MTS Assay

Cells were seeded in 10 cm TC dish and transfected with one of the following: pCMV-LIMK1-FLAG or pCMV control vector; LIMK1 shRNA vector or scrambled shRNA vector. 24 hrs post transfection cells were trypsinized and seeded into 96 well plates. Non-transfected cells were also seeded into the 96 well plates at the same time. After cells had adhered media was changed to complete media containing one of the following: 1 nM DTX, 2 nM DTX, 5 nM DTX; 10 nM PTX, 25 nM PTX, 50 nM PTX; or DMSO. At each time point MTS reagent was added to each well and allowed to incubate at 37° C. for 3 hrs before reading absorbances at 490 nM using Synergy H1 plate reader. Absorbance values were adjusted for background readings (620 nM), and then compared against control wells.

Flow Cytometry:

Cells were seeded into 60 mm dishes and transfected the following day with one of the previous constructs. 24 hrs post transfection, media was changed to complete media containing 2 nM DTX or 25 nM PTX. At each time point, media and cells were collected, washed, and fixed in 70% EtOH at −20° C. for at least 30 mins. Cells were then washed and stained for 30 mins in PBS containing: 2% BSA; 0.1% Pluronic F-68 (Sigma); Propidium Iodide [80 ug/mL] (Sigma); RNase [100 ug/mL]. Data was collected using FACSCalibur and analyzed using Cell Quest and ModFit software.

Annexin V Staining:

$1 \times 10^6$ cells were collected from flow cytometry samples before fixation. Cells were washed with cold PBS and resuspended in Binding Buffer (10 mM Hepes pH 7.4, 140 mM NaCl, 2.5 mM $CaCl_2$) at $1 \times 10^6$ cell/mL. 100 uL of cell solution were stained with 5 uL of Annexin V (BD Biosciences) and 10 uL PI [50 ug/mL] (Sigma). Cells were mixed and incubated at RT for 15 min in the dark. 400 uL of Binding buffer was added to each stained sample. Annexin V staining was quantified using FACSCalibur and data was analyzed using Cell Quest software.

Statistical Analysis.

Quantitative results from densitometry are presented as mean±SD of the number of independent experiments performed. Statistical differences were calculated using Student's t-test in GraphPad/Prism 4.0a. A p value of <0.05 was considered significant.

In reviewing the detailed disclosure which follows, and the specification more generally, it should be borne in mind that all patents, patent applications, patent publications, technical publications, scientific publications, and other references referenced herein are hereby incorporated by reference in this application in order to more fully describe the state of the art to which the present invention pertains.

Reference to particular buffers, media, reagents, cells, culture conditions and the like, or to some subclass of same, is not intended to be limiting, but should be read to include all such related materials that one of ordinary skill in the art would recognize as being of interest or value in the particular context in which that discussion is presented. For example, it is often possible to substitute one buffer system or culture medium for another, such that a different but known way is used to achieve the same goals as those to which the use of a suggested method, material or composition is directed.

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the following definitions are provided.

While a number of embodiments of the present invention have been shown and described herein in the present context, such embodiments are provided by way of example only, and not of limitation. Numerous variations, changes and substitutions will occur to those of skilled in the art without materially departing from the invention herein. For example, the present invention need not be limited to best mode disclosed herein, since other applications can equally benefit from the teachings of the present invention. Also, in the claims, means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

What is claimed is:

1. A pharmaceutical composition comprising a LIMK1 inhibitor and a chemotherapeutic agent in a pharmaceutically acceptable carrier wherein the LIMK1 inhibitor is an miRNA that targets LIMK1 RNA and disrupts gene expression of LIMK1.

2. The composition of claim 1, wherein said chemotherapeutic agent comprises a taxane.

3. The pharmaceutical composition of claim 1, wherein the pharmaceutical composition is formulated for intravenous administration, subcutaneous administration or topical administration.

4. The composition of claim 2, wherein said chemotherapeutic agent is less than 1.2 mg/ml taxane.

* * * * *

UNITED STATES PATENT AND TRADEMARK OFFICE
CERTIFICATE OF CORRECTION

PATENT NO. : 9,532,972 B2  
APPLICATION NO. : 14/376704  
DATED : January 3, 2017  
INVENTOR(S) : Ratna Chakrabarti It is certified that error appears in the above-identified patent and that said Letters Patent is hereby corrected as shown below:

In the Specification

Please add the following new paragraph after the TITLE and before the BACKGROUND paragraph.

--GOVERNMENT SUPPORT

This invention was made with Government support under agency contract/grant no. W81XWH-04-1-0874 awarded by the Army Medical Research and Material Command. The Government has certain rights in this invention.--

Signed and Sealed this  
Sixteenth Day of May, 2017

Michelle K. Lee  
*Director of the United States Patent and Trademark Office*